(12) United States Patent
Oi et al.

(10) Patent No.: US 8,220,632 B2
(45) Date of Patent: Jul. 17, 2012

(54) PACKAGED ABSORBENT PRODUCT HAVING TRANSLUCENT AREA

(75) Inventors: Kenji Oi, Kobe (JP); Nobuyuki Miki, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 512 days.

(21) Appl. No.: 11/796,509

(22) Filed: Apr. 27, 2007

(65) Prior Publication Data

US 2008/0011642 A1 Jan. 17, 2008

Related U.S. Application Data

(60) Provisional application No. 60/800,612, filed on May 16, 2006.

(51) Int. Cl.
*B65D 65/16* (2006.01)

(52) U.S. Cl. ............ 206/494; 206/459.5; 206/440

(58) Field of Classification Search .......... 206/494, 206/440, 776, 778, 524.1, 524.6, 812, 459.5; 383/106; 428/203–205
See application file for complete search history.

(56) References Cited

U.S. PATENT DOCUMENTS

| | | | |
|---|---|---|---|
| 1,844,189 A | 2/1932 | Stuart | |
| 3,306,437 A | 2/1967 | Nelson | |
| 3,351,209 A | 11/1967 | Kofoed et al. | |
| 3,988,499 A * | 10/1976 | Reynolds | 428/216 |
| 4,249,532 A | 2/1981 | Polansky et al. | |
| 4,479,995 A * | 10/1984 | Suzuki et al. | 428/203 |
| 4,556,146 A | 12/1985 | Swanson et al. | |
| RE32,443 E | 6/1987 | Kalal | |
| 4,696,050 A | 9/1987 | Sengewald | |
| 4,801,005 A | 1/1989 | Hahn | |
| 4,863,782 A * | 9/1989 | Wang et al. | 428/204 |
| 4,934,535 A | 6/1990 | Muckenfuhs | |
| 4,966,286 A | 10/1990 | Muckenfuhs | |
| D312,208 S | 11/1990 | Sorkin | |
| 4,991,980 A | 2/1991 | Cohen | |
| 5,044,492 A | 9/1991 | Auerbach | |
| 5,050,742 A | 9/1991 | Muckenfuhs | |
| 5,326,575 A | 7/1994 | Spaulding | |
| 5,344,027 A | 9/1994 | Kaplan | |
| 5,360,512 A | 11/1994 | Blum | |
| 5,361,905 A | 11/1994 | McQueeny | |
| D371,707 S | 7/1996 | Miles | |
| D372,272 S | 7/1996 | Frisch | |
| 5,569,228 A | 10/1996 | Byrd | |
| 5,630,512 A | 5/1997 | Wells | |

(Continued)

FOREIGN PATENT DOCUMENTS

DE 39 07 291 A1 9/1990

(Continued)

OTHER PUBLICATIONS

U.S. Appl. No. 11/796,508, filed Apr. 27, 2007, Kishida.

(Continued)

*Primary Examiner* — J. Gregory Pickett
*Assistant Examiner* — Andrew Perreault
(74) *Attorney, Agent, or Firm* — Andres E. Velarde

(57) ABSTRACT

A packaged absorbent product including at least one absorbent article having a body surface and a garment surface. The package includes a transparent film layer and a non-white color layer disposed on the transparent film layer. The package has an opacity of 5-55%, and a speculum gloss of 0.1-90.

19 Claims, 2 Drawing Sheets

U.S. PATENT DOCUMENTS

| | | | |
|---|---|---|---|
| 5,743,407 | A | 4/1998 | Williams |
| 5,834,077 | A * | 11/1998 | Babrowicz .................. 428/34.9 |
| 5,839,585 | A | 11/1998 | Miller |
| 5,865,322 | A | 2/1999 | Miller |
| 5,897,541 | A * | 4/1999 | Uitenbroek et al. .......... 604/358 |
| 5,897,542 | A | 4/1999 | Lash |
| 5,924,559 | A | 7/1999 | Carrel |
| 5,931,304 | A | 8/1999 | Hammond |
| 5,947,297 | A | 9/1999 | Aoki |
| 5,947,302 | A | 9/1999 | Miller |
| 5,967,665 | A | 10/1999 | MacDonald |
| 5,972,473 | A * | 10/1999 | Arakawa et al. .............. 428/141 |
| 6,074,376 | A | 6/2000 | Mills |
| 6,077,579 | A | 6/2000 | De Laforcade |
| 6,093,027 | A | 7/2000 | Unger et al. |
| 6,152,305 | A | 11/2000 | Green |
| 6,168,028 | B1 | 1/2001 | Telesca |
| 6,318,555 | B1 * | 11/2001 | Kuske et al. ................... 206/494 |
| 6,368,113 | B1 | 4/2002 | Unger et al. |
| 6,368,758 | B1 * | 4/2002 | Camp et al. ...................... 430/12 |
| 6,454,095 | B1 | 9/2002 | Brisebois et al. |
| 6,457,585 | B1 * | 10/2002 | Huffer et al. ................ 206/459.5 |
| 6,601,705 | B2 * | 8/2003 | Molina et al. .................. 206/494 |
| 6,612,846 | B1 | 9/2003 | Underhill et al. |
| 7,571,810 | B2 * | 8/2009 | Tilton ............................ 206/462 |
| 7,832,560 | B2 * | 11/2010 | Tilton ............................ 206/462 |
| 2002/0046079 | A1 | 4/2002 | Stavrulov |
| 2004/0071994 | A1 | 4/2004 | Busch et al. |
| 2004/0102748 | A1 | 5/2004 | Hirotsu |
| 2005/0145523 | A1 | 7/2005 | Zander et al. |
| 2005/0209576 | A1 | 9/2005 | Hirotsu |
| 2005/0261655 | A1 | 11/2005 | Nijs et al. |
| 2007/0108078 | A1 | 5/2007 | Molina et al. |
| 2007/0131570 | A1 | 6/2007 | Nijs et al. |
| 2007/0179467 | A1 * | 8/2007 | Shimizu et al. .......... 604/385.02 |

FOREIGN PATENT DOCUMENTS

| | | |
|---|---|---|
| EP | 0 986 996 A2 | 3/2000 |
| EP | 1 174 104 A1 | 1/2002 |
| EP | 1 153 838 B1 | 10/2004 |
| EP | 1 767 377 A1 | 3/2007 |
| WO | WO 93/16929 A1 | 9/1993 |
| WO | WO 96/22756 A2 | 8/1996 |
| WO | WO 97/49618 A2 | 12/1997 |
| WO | WO 2006/069653 A | 7/2006 |

OTHER PUBLICATIONS

U.S. Appl. No. 11/650,822, filed Jan. 8, 2007, Molina et al.
PCT International Search Report dated Dec. 9, 2007.
HTTP://MUM.ORG/FREEDBOX.HTM—Box of Tampons at the Museum of Menstruation and Women's Health—2 pages.
Product Images on CD.

* cited by examiner

PACKAGED ABSORBENT PRODUCT HAVING TRANSLUCENT AREA

CROSS REFERENCE TO RELATED APPLICATION

This application claims the benefit of U.S. Provisional Application No. 60/800,612 filed on May 16, 2006.

FIELD OF THE INVENTION

The present invention relates to packaged absorbent products. More particularly, the present invention relates to a packaged absorbent product having a translucent area(s) on the package.

BACKGROUND OF THE INVENTION

Absorbent articles such as sanitary napkins, pantiliners, baby diapers, and incontinent diapers and pads are devices that are typically worn in the crotch region of an undergarment. More specifically, sanitary napkins and pantiliners, for example, are worn by women in a pair of panties that is normally positioned between the wearer's legs, adjacent to the perineum area. These are designed to absorb and retain body fluids or discharges (e.g., menses and urine) from the body of women and to prevent body and clothing from soiling. These absorbent articles are stacked and contained in a package for shipping and sale.

Recent developments for disposable absorbent articles tend to focus on not only improvement of their pad functions (e.g., superior absorbency, leakage protection and comfort) but their aesthetic features. This trend is true for both pads and package aesthetics. For example, absorbent articles which have an aesthetic feature is disclosed in WO 2004/006818 published on Jan. 24, 2004.

Package aesthetics for disposable absorbent articles are important since it may affect a consumer's impression at the shelves in stores and motivation for purchase. For this reason, package aesthetics have been becoming one of important product features in the recent market of disposable absorbent articles. It is believed that superior aesthetics can provide "premium impression" which tends to promote consumer's high motivation for purchase. However, conventional packaged disposable absorbent products tend not to provide consumers with enough premium impression by their appearance.

Thus, there is a need for a packaged absorbent product that can provide premium impression thereby promoting consumers' motivation for purchase.

SUMMARY OF THE INVENTION

The invention is directed to a packaged absorbent product, comprising: (a) at least one absorbent article having a body surface and a garment surface; and (b) a package for containing the absorbent article therein. The package is formed by a package member. The package member includes a transparent film layer and a non-white color layer disposed on the transparent film layer. The package member has an opacity of 5-55%, and a speculum gloss of 0.1-90.

The foregoing answers the need for a packaged absorbent product that can provide premium impression thereby promoting consumers' motivation for purchase.

These and other features, aspects, and advantages of the present invention will become evident to those skilled in the art from reading of the present disclosure.

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include sanitary napkins, pantiliners, tampons, interlabial devices, diapers (both for baby and adult incontinent), and adult incontinent pads (and other articles worn in the crotch region of a garment).

Herein, "disposable" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine).

Herein, "package" refers to means which contains an absorbent article(s). Packages are formed by a package member. The package can take any structure known in the art. In certain embodiments, material(s) for the package member can be liquid and moisture impermeable so that the package can protect the stored absorbent articles from being affected by the moisture outside of the package. One typical example of such a package can be a flexible plastic film bag or a cardboard box which contains a plurality of absorbent articles. Such a package is commonly used in many countries since it can contain many absorbent articles. Another example of such a package can be an individual wrapper or a pouch which contains each or a single absorbent article. Specifically, in recent disposable absorbent articles (typically sanitary napkins and pantiliners), each pad is folded and wrapped individually by a wrapper sheet, or contained in a pouch. One example of individual wrapping structure for sanitary napkins having a pair of flaps is disclosed in U.S. Pat. No. 6,074,376 issued to Mills on Jun. 13, 2000.

Herein, "graphic" refers to a pattern that is constituted by a figure(s) (i.e., a line(s)), a symbol(s) or character(s), a color difference or transition of at least two colors, and the like. In certain embodiments, the graphic has an aesthetic design and/or color that can provide emotional benefit(s) when the absorbent article having the graphic is looked or viewed by consumers. The graphic may include other element(s), for example, an information tip(s) such as the usage information and the size of the absorbent article, an indication of the front/back of the absorbent article, a brand name or logo of the absorbent article, and the like. The graphic can be typically formed by a printing process known in the art.

Figure 1:
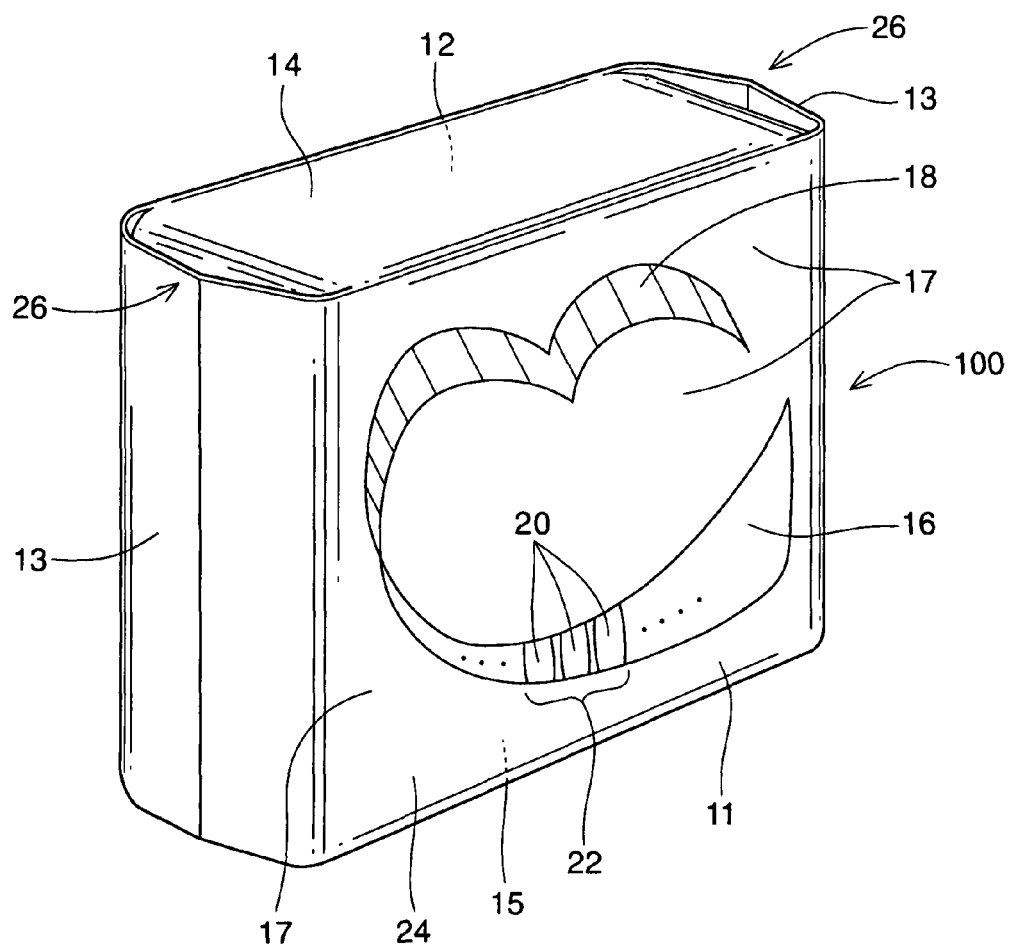
FIG. 1 is a simplified perspective illustration of a package for disposable absorbent articles, which is one embodiment of the present invention.
Figure 2:
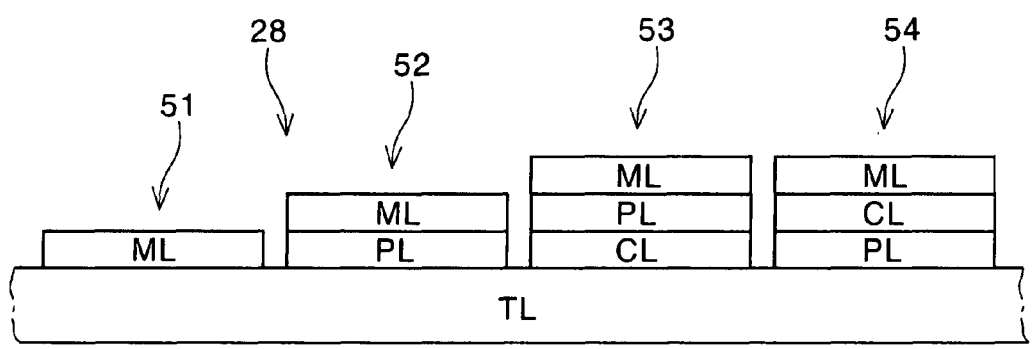
FIG. 2 is a cross-sectional view of a package member which shows embodiments of the present invention.
Figure 3:
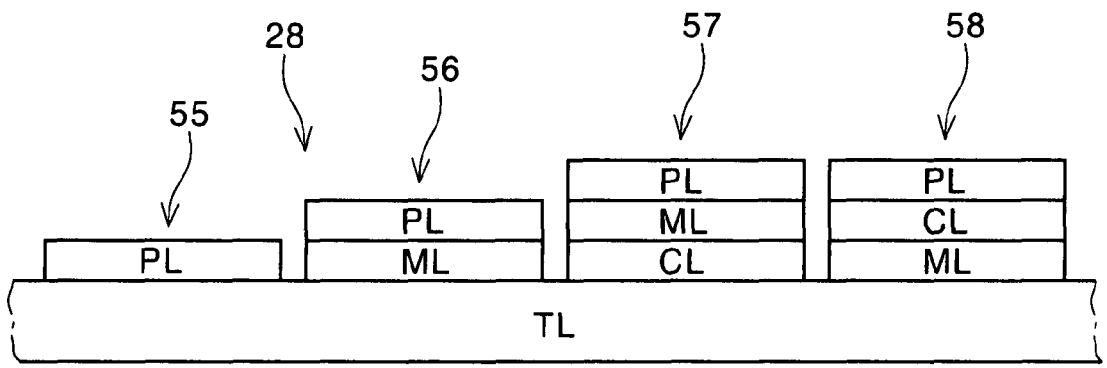
FIG. 3 a cross-sectional view of another package member which shows additional embodiments of the present invention.
Figure 4:
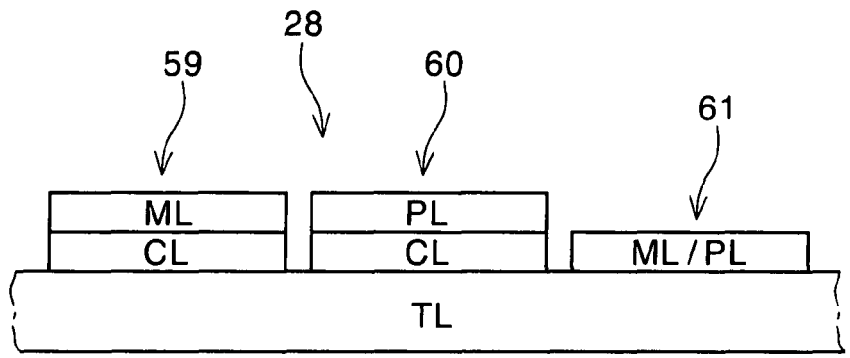
FIG. 4 is a cross-sectional view of an yet another package member which shows further embodiments of the present invention.

FIG. 1 is a simplified perspective illustration of a package 100 for disposable absorbent articles 20 (i.e., a packaged absorbent product), which is one embodiment of the present invention. In this embodiment, the package 100 contains a plurality of disposable absorbent articles 20. These disposable absorbent articles 20 can be stacked to form at least one stack 22 in the package 100.

The package 100 includes a front panel 11, a rear panel 12 opposed to the front panel 11, side panels 13 which connects the front and rear panels 11 and 12, a top panel 14 which connects the front, rear, and side panels 11, 12 and 13, and a bottom panel 15 opposed to the top panel 14. Each pair of the front and rear panels 11 and 12, the side panels 13 and the top and bottom panels 14 and 15 can be substantially planar as shown in FIG. 1. These panels 11-15 form an outer surface 24 of the package 100.

The package 100 shown in FIG. 1 can be a flexible bag which can be formed from a continuous tube of a thin plastic film material. The side portions of the package 100 can be closed by forming gusset structures 26 at the side panels 13. In the embodiment shown in FIG. 1, a polyethylene film can be used as a base film material of a package member.

The package 100 may include the same type, design and size of disposable absorbent articles 20. Alternatively, if desired, it may include two (or more) different types, designs and/or sizes of absorbent articles 20. In certain embodiments, the package 100 contains the same type, design and size of feminine hygiene articles such as sanitary napkins and pantiliners.

In certain embodiments, at least some of the disposable absorbent articles 20 includes either an individual flexible wrapper structure or a pouch structure which wraps or contains the respective absorbent article. Further, some or all of the disposable absorbent articles 20 can be just stacked and stored in the package 100 without being individually wrapped or contained by a flexible wrapper or pouch.

Each of the disposable absorbent articles 20 can be stored in the package 100 with or without being folded. In certain embodiments, at least a part of each disposable absorbent article can be folded inwardly. The folding operation for the absorbent articles 20 can be typically carried out before or when they are stored in the package 100 or the flexible wrapper or pouch. For example, when the disposable absorbent articles 20 are sanitary napkins, each sanitary napkin can be folded along one or two (or more if desired) folding lines so that the sanitary napkin can be folded into at least two (or three) sections which are defined by the folding line(s). Examples of the manners for folding and/or wrapping feminine hygiene articles (e.g., sanitary napkins) are disclosed in U.S. Pat. No. 6,074,376 issued to Mills on Jun. 13, 2000 and U.S. Pat. No. 5,569,228 issued to Byrd et al. on Oct. 29, 1996.

The package 100 has at least an area(s) or a portion(s) 17 which is translucent (hereinafter referred to "translucent area"). Such an translucent area(s) 17 can be formed in any panels of the package 100. In certain embodiments, the translucent area(s) 17 can be formed in at least in the front panel 11, and if desired, one or more additional panels. Although the translucent area(s) 17 can occupy the whole area on one panel, it can also occupy a part of the panel so that the panel can have a non-translucent or non-transparent area(s) 18. The existence of such a non-translucent or non-transparent area(s) 18 is beneficial since it can clearly indicate graphic(s) and/or product information such as a brand name, a product name, a functional explanation, a product usage explanation, and the like. In addition, the co-existence of the translucent area(s) 17 and the non-translucent or non-transparent area(s) 18 is also beneficial since it can show a unique contrast on the package appearance which can cause consumers' additional attention at the shelves in stores.

In certain embodiments, the package member (or the package 100) includes, in an translucent area(s) 17, a transparent film layer (or a base film layer) and a non-white color layer disposed on the transparent film layer. In other words, the translucent area 17 can be formed by the transparent film layer and the non-white color layer disposed on the transparent film layer. In one embodiment, the package member has an opacity of 5-55%, and a speculum gloss of 0.1-90 in the translucent area 17. In another embodiment, the package member has an opacity of 15-40% and a speculum gloss of 2-15 in the translucent area 17.

Herein, "disposed" encompasses configurations in which an element is directly placed to another element; and configurations in which the element is indirectly placed to the other element by placing the element to an intermediate element(s) which in turn is placed to the other element.

Herein, "transparent film layer" refers to a single layer or a plurality of layers that contains a thermoplastic polymer(s) and a limited amount of a pigment(s) and a filler(s) such that the resultant layer has an opacity of 0.1-50%. The opacity of the transparent film layer can be controlled by the amount of the filler(s). In certain embodiments, the resultant layer has an opacity of 1-20%.

Herein, "non-white color layer" refers to a single layer or a plurality of layers which is formed by a thermoplastic polymer(s) or an ink(s) that contains no more than 25% of a filler which is selected from the group consisting of a titanium dioxide, a zinc oxide, a calcium carbonate, or the mixture thereof. When the non-white color layer is formed by a thermoplastic polymer(s), such a thermoplastic polymer layer a limited amount of a pigment(s) and/or a filler(s). Alternatively, when the non-white color layer is formed by an ink(s), such an ink layer can be typically formed by a printing process as described hereinafter.

The materials for a pigment(s) and/or a filler(s) which can be used in the transparent film layer and the non-white color layer can be typically in the form of a particle. Such particles can be dispersed in the thermoplastic polymer in the transparent film layer and the non-white color layer.

By giving the aforementioned ranges of opacity and speculum gloss to the package member, the package 100 using the package member can produce a translucent area 17 which premium impression thereby promoting consumers' motivation for purchase of the absorbent articles 20.

The optical properties of the package member include the opacity (OP) and the speculum gloss (Gs). The methods for measuring these optical properties of a package member is described in the "TEST METHODS" section.

The opacity of a package member shows the degree of un-clearness or un-transparency of the package member. When a package member has an opacity of 0%, the package member can be completely transparent. On the other hand, if a package member has an opacity of 100%, the package member has no transparency, i.e., no light can be transmitted through the material. The opacity of the package member shows the degree on how clearly the absorbent article(s) packaged by the package member can be seen through the package member. In general, when the opacity of the package member material is within certain lower range (e.g., 5-50%), it helps the user to see features of the absorbent article(s) through the package member.

Such features include the type (e.g., thickness or thinness), graphic, color of the absorbent article, and the like. When the absorbent article has a feature on its appearance, such a feature can be recognized through the package member. For example, when the absorbent article contained the package 100 has an atheistic feature such as a graphic, the feature can be seen through the package member. This means that the packaged absorbent article can provide the graphic benefit without printing the graphic on the package 100. This results in a decrease of the material cost for the package member since it can eliminate the need of printing graphics on the package member. In another example, when at least one edge of the absorbent article faces the translucent area 17 of the package 100, the thickness of the absorbent article can be seen through the package member. Thus, consumers who are going to purchase the absorbent article in the market can easily recognize the type of absorbent article with an actual image (e.g., the thick type or the slim type in case of sanitary napkin) contained in the package 100.

The speculum gloss of a package member affects an impression of the package member, in particular the impression of appearance, texture/touch, tactile of the package member that eventually affect the value and quality impression. In general, when the speculum gloss of the package member is within certain lower range (e.g., 0.1-12), it can also provide some emotional benefit(s) such as soft image of the product (e.g., soft appearance image, soft texture/touch image, and soft tactile image). For example, when the package member has an opacity of 5-55%, and a speculum gloss of 0.1-90 (i.e., a combination of low values of the opacity and the speculum gloss), the package member may provide premium impression of the product since it can produce high quality image, sophisticated image and/or fresh/newness image.

In addition, since transparent package members clearly show the contents of the package, consumers of feminine hygiene articles tend to feel ashamed when purchase in the market. In addition, transparent package members may give consumers a cheap impression. On the contrary, since non-transparent package members can not show the contents of the package, the aesthetic feature of the contents can not be seen by consumers of feminine hygiene articles. The present invention can resolve such a dilemma. Since the package member has the low values of the opacity and the speculum gloss, people who have no particular attention can not see the contents quickly, however, those who have particular attention to the contents can see the aesthetic feature of the contents by itself or can clearly see it by making the package member to contact by pushing slightly. Thus, the packaged absorbent article formed by the package member having such lower ranges of the opacity and the speculum gloss can promote consumers' motivation for purchase.

The opacity and the speculum gloss of the package member can be controlled by changing the kinds and amount of ingredients contained in the non-white color layer, and/or if desired, a surface treatment at the non-white color layer and/or the transparent film layer, as described hereinafter.

Figure 5:
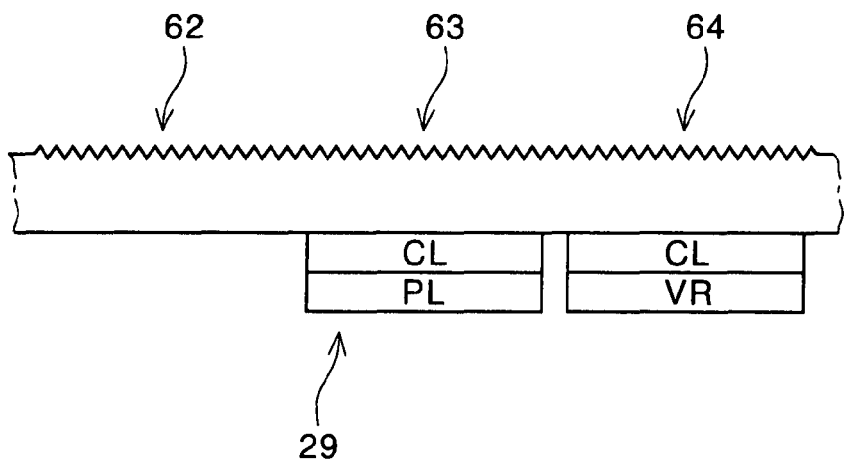
FIG. 5 is a cross-sectional view of a still another package member which shows still further embodiments of the present invention.

FIGS. 2-5 are cross-sectional views of package members which show various embodiments of the present invention. In FIGS. 2-5, the transparent film layer, the matte layer, the pearl layer and the color layer are indicated by "TL", "ML", "PL" and "CL", respectively. In FIG. 5, the varnish layer is indicated by "VR". In FIGS. 2-5, the upper surface 28 corresponds to the outer surface 24 of the package 100.

In certain embodiments, the non-white color layer includes a matte layer disposed on the transparent film layer (i.e., the structure 51). The non-white color layer can further include a pearl layer disposed between the transparent film layer and the matte layer (i.e., the structure 52). In certain embodiments, the non-white color layer can further include a color layer disposed between the transparent film layer and the peal layer (i.e., the structure 53). This configuration may increase the pearl effect produced by the pearl layer effectively while keeping the translucency as designed, yet the color control is difficult. Alternatively, such a color layer can be disposed between the pearl layer and the matte layer (i.e., the structure 54). This configuration can soften the pearl effect by the matte layer disposed on the pearl layer, yet the color control is easy.

Herein, "color layer" is a part of the non-white color layer. The color layer refers to a single layer or a plurality of layers formed by a thermoplastic polymer(s) or an ink(s) that contains a pigment(s) which defines to the target color of the package member.

In an alternative embodiment, the non-white color layer includes a pearl layer disposed on the transparent film layer (i.e., the structure 55). The non-white color layer can further include a matte layer disposed between the transparent film layer and the pear layer (i.e., the structure 56). In certain embodiments, the non-white color layer can further include a color layer disposed between the transparent film layer and the matte layer (i.e., the structure 57). Alternatively, such a color layer can be disposed between the matte layer and the pearl layer (i.e., the structure 58).

In an yet another embodiment, the package member can include and be formed by a matte layer and a color layer disposed between the transparent film layer and the matte layer (i.e., the structure 59). Alternatively, the package member can include and be formed by a pearl layer and a color layer disposed between the transparent film layer and the pearl layer (i.e., the structure 60).

If desired, the matte layer and the pearl layer can be formed by a single layer (i.e., the structure 61). Such a single layer can be formed by mixing the component materials which are typically contained in the matte layer and the pearl layer with a thermoplastic polymer(s) or an ink(s).

Alternatively, the matte layer can be formed by a surface treatment at one surface of the transparent film layer (i.e., the structures 62-64) which is described hereinafter. In certain embodiments, the non-white color layer includes a matte layer disposed on one surface (i.e., the upper surface 28) of the transparent film layer (i.e., the structure 62). In certain embodiments, the non-white color layer can further include a color layer disposed on the other surface (i.e., the upper surface 29) of the transparent film layer (i.e., the structures 63 and 64). The non-white color layer may further include a pearl layer disposed on the color layer (i.e., the structure 63). Alternatively, the non-white color layer can further include a varnish layer disposed on the color layer (i.e., the structure 64), which protects the color layer.

In certain embodiments, package members for the aforementioned bag, box, individual wrapper and pouch typically include (or can be formed by) a thin film material formed by a thermoplastic polymer(s). Such package members can be biodegradable, non-biodegradable, non-recyclable, or recyclable.

Suitable thermoplastic polymers for the package member (in particular for the base film layer) include polyolefin such as polyethylene (PE), including a liner low density polyethylene (LLDPE), a low density polyethylene (LDPE), a ultra low density polyethylene (ULDPE), a high density polyethylene (HDPE), a polypropylene, and a mixture thereof. Other suitable thermoplastic polymers which may also be used include, but are not limited to a polyester, a polyurethane, a compostable or biodegradable polymer, a thermoplastic elastomer, and a metallocene catalyst-based polymer.

In certain embodiments, the package member can be formed by a polyolefin film formed by polyethylene or polypropylene. In the embodiment shown in FIG. 1, the package 100 can be a flexible bag which can be formed by a polyethylene film as a transparent film layer (or a base film material).

The material for the filler can be an inorganic material which can be selected from the group consisting of a titanium dioxide, a zinc oxide, a calcium carbonate, Silicon dioxide, a mica and a mixture thereof. Alternatively (or if desired), the material for the filler can be an organic material such as a high-density polyethylene or other organic polymer material such as a polypropylene.

In a manufacture process, the thermoplastic polymer, filler and pigment can be mixed or blended together to form a homogeneous mixture in a suitable mixing extrude, or in a separate preliminary compounding step. The mixture can be then cast or blown into a film or a nonwoven web.

The amount of the filler may affect the opacity level of the package member. For example, increasing the filler material may make the resultant material more opaque, while decreasing the filler material may make the resultant material more transparent. Thus, the opacity level of the package member may be controlled by changing the amount fillers contained in the package member material.

In certain embodiments, the speculum gloss level of the package member can be controlled by a surface treatment at at least one surface(s) of the component layer(s) of the package member. Such a surface treatment can be either physical or chemical. The surface treatment produces a lumpy or irregular surface(s) which affects the speculum gloss level of the package member.

In certain embodiments, the surface treatment can be a micro emboss treatment (i.e., a physical surface treatment) formed at at least one surface(s) of the transparent film layer or the non-white color layer of the package member. Herein, "micro emboss treatment" is a physical treatment at a surface of a film material that produces a change of the speculum gloss level at the surface of the film material thereby causing a matte effect which can be brought by the matte layer.

In one embodiment, after the formation of a package member material, such a micro emboss treatment can be implemented to produce a package member having a matte texture. Such a micro emboss treatment can be implemented during a casting process by nipping at a casting machine at a casting process. Alternatively, such a micro emboss treatment can be implemented by embossing after re-heating the package member material in a blowing process or in a casting process. Alternatively, this micro emboss could be delivered by adding the forming agents.

In an alternative embodiment, the surface treatment can be a chemical treatment (i.e., a chemical surface treatment) formed at at least one surface(s) of the component layer(s) of the package member. Herein, "chemical treatment" is a surface treatment by a chemical agent which produces a change of the speculum gloss level at the surface of the film material thereby causing a matte effect which can be brought by the matte layer.

In certain embodiments, the pearl layer includes a thermoplastic polymer and a filler that produces a pearl effect. Herein, "pearl effect" refers to a visual effect which gives material the "pearly" or "glitter" appearance. The pearl effect can be brought by adding pearl particles into the film ingredient(s), i.e., the thermoplastic polymer. In one embodiment, pearl particles include a mica powder or an iriodine powder.

In certain embodiments, a mica can be used as the filler to produce a package member material having a peal effect. In one embodiment, the mica has an average diameter of about 5-25 microns and is available from, for example, Shinhwa Corporation, Korea, under the Local Tracking Number 2006-0466-01.

Any layer of the non-white color layer can include a pigment(s) which can be mixed with the thermoplastic polymer and/or the filler so that the package member can produce a primary color. The pigment(s) should be selected depending on the target color. An appropriate selection of a pigment(s) contributes to a production of a package member having an expected non-white color (e.g., blue, red, yellow, green, gray, etc). It should be noted that depending the color, the amount of the pigment can affect the opacity level of the film material.

In alternative embodiments, the optical properties of the package member can be also controlled by a non-white color layer which can be formed by an ink printing on the transparent film layer. More specifically, the opacity level and the speculum gloss of the package member can be controlled by a printed ink layer (as a non-white color layer) disposed on the transparent film layer. Such a printed ink layer can be formed by changing the kinds and amount of ingredients of the ink(s) to be used for printing the surface of the package member.

Such a printed ink layer can be formed by any conventional printing methods known in the art such as a gravure printing, a flexography printing, a letter press printing, an offset printing, an ink jet printing, and the like. Typically, a printing ink contains about 60% of a binder resin, about 40% of a pigment (or dye), and a very small amount of additives such as process aid(s) which are typically used for drying up the solvents after the printing process.

The opacity level of the package member can also be controlled by the kinds and amount of ingredients of the printing ink(s). In order to increase the opacity level of the package member, an ink which contains an inorganic pigment(s) such as a titanium dioxide, a zinc oxide, a calcium carbonate, silicon dioxide, mica, and the like can be used. Such inorganic pigment(s) can provide higher opacity by increasing its amount. The particle size of the inorganic pigment(s) can vary depending on the printing method to be employed. In one embodiment, a titanium dioxide can be used as the pigment.

In certain embodiments, the matte layer can be formed by printing, i.e., forming an ink layer disposed on the transparent film layer. Such a printed ink layer can include an inorganic or organic contaminant(s) in the printing ink(s) or layer(s). The average particle size of such contaminant(s) can be selected such that it can make the printed surface mat and rough enough to provide the same or similar effect given by the micro emboss treatment. The average particle size of such contaminant(s) can vary depending on the printing method to be employed. In one embodiment, the average particle size of such contaminant(s) are in a range of 0.1-100 microns. In certain embodiments, particles of a mixture of silicon dioxide, mica and titanium dioxide can be used.

In certain embodiments, the package member further includes a pearl layer (as an optical treatment layer) disposed between the transparent film layer and the matte layer. The peal layer can be formed by printing an ink layer on the transparent film layer. Such a printed ink layer includes a thermoplastic polymer and a filler that produces a pearl effect. In this embodiment, the pearl effect can also be produced by introducing pearl particles in the printing ink(s) or layer(s). In certain embodiments, pearl particles can be formed by a mica or an iriogine. These pearl particles can give the printed surface a pearly appearance which can be enough to provide the same or similar effect to those given by the above described embodiment employing the thermoplastic polymer and the filler.

The average particle size of such pearl particles can vary (e.g., about 1-100 microns) depending on the printing method to be employed. In one embodiment, a mica which has an average particle size of 5-25 microns can be used. In another embodiment, the speculum gloss and opacity level of the package member can be controlled by the amount of the pearl particles.

In certain embodiments, the printed ink layer forms a color layer which includes a pigment(s) mixed with the ink ingredient(s) so that the package member can produce a target color. The kinds and amount of ingredients of the ink(s) should be selected depending on the target color. An appropriate selection of a pigment(s) contributes to a production of a package member having an expected non-white color. It should be noted that depending the color, the amount of the pigment can affect the opacity level of the film material.

Examples of package member materials are shown in Table 1 below. Each "Structure" indicated in Table 1 corresponds to the respective structure shown in FIGS. 2-4.

be provided in the front or the other panel(s) of the package 100. For example, an additional window(s) may be provided in the rear panel 12 and/or the side panels 13. Or, if desired, the window 16 can be extended from one panel to another adjacent panel(s).

The window 16 can take any shape such as a circle, a square, a rectangle, a trapezoid, an ellipse, a triangle or any other shape such as shown in FIG. 1. The window 16 can have any sizes or dimensions. In one embodiment, the window 16 has an enough dimension (e.g., the length and the width for a rectangular window) so that at least some of the contained absorbent articles 20 can be seen through the window 16.

Since the disposable absorbent articles 20 contained in the package 100 can be seen by users through the window 16, users can consume the plurality of types of disposable absorbent articles 20 equally. The window 16 also enables consumers (or purchasers) to see the design of the contained disposable absorbent articles 20 in the package 100. This is

TABLE 1

| Sample No. | Material | Code No. | Supplier | OP (%) | Gs | Thickness (micron) |
|---|---|---|---|---|---|---|
| 0 | TL only | 2006-0465-01 | Taiwan Lianbin | 4 | 85 | 50 |
| 1-1 | TL + ML (Structure 51) | 2006-0465-01 | Taiwan Lianbin | 19 | 6 | 50 |
| 1-2 | TL + CL (PG 371 - yellow) + ML (Structure 59) | 2006-0465-01 | Taiwan Lianbin | 32 | 6 | 50 |
| 1-3 | TL + CL (PG582 - blue) + ML (Structure 59) | 2006-0465-01 | Taiwan Lianbin | 29 | 6 | 50 |
| 1-4 | TL + WL + CL (PG582 - blue) + ML | 2006-0465-01 | Taiwan Lianbin | 59 | 3 | 50 |
| 2-1 | TL + PL + ML (Structure 52) | 2006-0466-01 | Taiwan Lianbin | 32 | 6 | 50 |
| 2-2 | TL + CL (PG737 - light green) + PL + ML (Structure 53) | 2006-0466-01 | Taiwan Lianbin | 44 | 6 | 50 |
| 2-3 | TL + CL (PG398 - dark green) + PL + ML (Structure 53) | 2006-0466-01 | Taiwan Lianbin | 54 | 5 | 50 |
| 2-4 | TL + WL + CL (PG398 - dark green) + PL + ML | 2006-0466-01 | Taiwan Lianbin | 82 | 6 | 50 |
| 3 | TL + CL (PG023 - cyan) + ML (Structure 59) | 2006-0437-01 | Fujiko | 21 | 8 | 40 |
| 4 | TL with micro emboss (Structure 62) | Borstar BF2230 | Shanghai Lianbin | 10 | 11 | 50 |

Notes:
1) OP: Opacity (%); Gs: Speculum Gloss
2) Matte layer (ML) contains a silicon dioxide.
3) Pearl layer (PL) contains a mica.
4) Transparent film layer (TL) is formed by polyethylene.
5) Sample Nos. 0, 1-4 and 2-4 are for reference purpose.
6) Sample Nos. 1-4 and 2-4 contain a white ink layer (WL).

In one embodiment, the package 100 has a transparent window 16 which shows at least one (or more if desired) of the absorbent articles 20 contained in the package 100 through the window 16. Herein, "transparent window" refers to a transparent area(s) or a portion(s) which is formed on one panel of the package and can show at least a part of the absorbent article(s) contained in the package therethrough. The transparent window can have a color and/or some translucency but it should have enough transparency so that an outline of the absorbent article(s) contained in the package can be seen clearly.

The window 16 can be provided at any panels of the package 100 but, in certain embodiments, it is provided in at least the front panel 11. If desired, a plurality of the windows may beneficial at the point of purchase in particular when an attractive graphic(s) is printed at a part of the contained disposable absorbent articles 20.

The window 16 can be formed by any means known in the art. In certain embodiments, the window 16 can be formed by differentiating the transparency at the window 16 from the surrounding area of the window 16. Such a differentiation can be made by using different inks between the area within the window 16 and the area surrounding the window 16. In the embodiment shown in FIG. 1, the window 16 can be formed by applying no paint in the area of the window 16 so that it has a very high transparency, while applying a paint which makes the surrounding area of the window 16 non-transparent. The rest of the front panel 11 can have one or more colors as well as lines, patterns, ornamental designs, pictures, symbols, characters (or codes), and the combination thereof.

Test Methods

This section describes methods for determining an opacity and a speculum gloss.

I. Opacity (OP)

A dispersion colorimeter can be used for determining the opacity of a sample material. One example of such a dispersion calorimeter is available from BYK-Gardner GmbH, Geretsried, Germany, under Trade Name "BYK Gardner Color-Guide 45/0" (Cat. No. 6800).

The measurements should be conducted by using a light source "A" at a viewing angle of 2° (degrees).

This dispersion colorimeter includes a light source for Illuminant A (i.e., an approximation of incandescent lamp having a correlated color temperature of about 3000 K), a flat table, a white standard plate, a standard black plate, a photo detector which includes a multi-celled photo-detector diode array, and a computer. The white and black standard plates are available from the same company under Cat. Nos. 6811 and 6810, respectively.

In the measurement, the white standard plate is placed on the flat table. A sample material is put on the white standard plate in a flat state. The sample material is illuminated by the light source with an incident angle of 45°. The reflection light which is reflected from the sample material is received by the photo detector with a receiving angle of 0°. The reflection rate (Yw) of the reflection light is detected by the photo detector. Similarly, after the black standard plate is placed on the flat table, the sample material is put on the black standard plate in a flat state. The sample material is illuminated by the light source with an incident angle of 45°. The reflection light which is reflected from the sample material is received by the photo detector with a receiving angle of 0°. The reflection rate (Yb) of the reflection light is detected by the photo detector.

The opacity (OP) is obtained by the following formula:

$$OP(\%) = (Yb/Yw) \times 100 \qquad (1)$$

This process is repeated for one sample package member at least five times and the average value of the opacities (OP) measured is calculated and recorded by the colorimeter. The average value of the opacities measured is called the opacity of a package member.

II. Speculum Gloss (Gs)

A gloss meter is used for determining the speculum gloss of a sample material. One example of such a gloss meter is available from K. K. Horiba, Kyoto, Japan, under Trade Name "Handy Gloss Checker" (IG-330).

This gloss meter includes a light source for Illuminant A (i.e., an approximation of incandescent lamp having a correlated color temperature of about 3000 K), a flat table, a black glass plate (as the calibration standard plate), a photo detector which includes a photo-detector, and a computer. The black glass plate has a predetermined speculum gloss ($G_0$=90) under 60 degrees system.

Before starting the measurement, the gloss meter is calibrated by using the calibration standard plate. I.e., the measuring instrument which has a light source and a photo detector is put on the calibration standard plate in a flat state. The calibration standard plate is illuminated by the light source with an incident angle of 60°. The reflection light which is reflected from the sample material is received by the photo detector with a receiving angle of 60°. The intensity ($\phi o$) of the reflection light is detected by the photo detector.

In the measurement, the calibrated measuring instrument is put on the a sample material in a flat state. The sample material is illuminated by the light source with an incident angle of 60°. The reflection light which is reflected from the sample material is received by the photo detector with a receiving angle of 60°. The intensity ($\phi s$) of the reflection light is detected by the photo detector and the speculum gloss (Gs) is calculated and obtained using following formula by the equipment $$Gs = (\phi s/\phi o) \times G_0 \qquad (2)$$

$G_0$ is the speculum gloss of the standard plate ($G_0$=90)

This process is repeated for each material at least five times and the average value of the speculum gloss (Gs) measured is calculated and recorded by the computer. The average value of the speculum gloss measured is called the speculum gloss of a package member.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A packaged absorbent product, comprising:
   (a) at least one absorbent article having a body surface and a garment surface; and
   (b) a package for containing the absorbent article therein, the package being formed by a package member;
   the package member including a transparent film layer and a non-white color layer disposed on the transparent film layer wherein said non-white layer is selected from the group consisting of a matte layer, a pearl layer, and a combination of a matte layer and a pearl layer;
   the package member having an opacity of 15-40%, and a speculum gloss of 2-15; wherein the transparent film layer and the non-white color layer comprise a thermoplastic polymer selected from the group consisting of a polyethylene, a liner low density polyethylene, a low density polyethylene, a ultra low density polyethylene, a high density polyethylene, a polypropylene, a polyester, a polyurethane, a compostable or biodegradable polymer, a metallocene catalyst-based polymer, and combinations thereof.

2. The packaged absorbent product of the claim 1, wherein the package member has a pearl layer disposed between the transparent film layer and the matte layer.

3. The packaged absorbent product of the claim 2, wherein the non-white color layer further includes a color layer disposed between the pearl layer and the matte layer.

4. The packaged absorbent product of the claim 1, wherein the non-white color layer further includes a color layer disposed between the transparent film layer and the matte layer.

5. The packaged absorbent product of the claim 1, wherein the non-white color layer further includes a color layer disposed between the transparent film layer and the pearl layer.

6. The packaged absorbent product of the claim 1, wherein the matte layer is formed by a micro emboss treatment at one surface of the transparent film layer.

7. The packaged absorbent product of the claim 6, wherein the non-white color layer further includes a color layer disposed on the other surface of the transparent film layer.

8. The packaged absorbent product of the claim 7, wherein the non-white color layer further includes a pearl layer disposed on the color layer.

9. The packaged absorbent product of the claim 1, wherein the package has a pouch structure or an individual wrapper structure for containing the absorbent article.

10. A packaged absorbent product, comprising:
 (a) at least one absorbent article having a body surface and a garment surface; and
 (b) a package for containing the absorbent article therein, the package being formed by a package member;
 (c) the package member including a transparent film layer and a non-white color layer disposed on the transparent film layer; said package member having a printed ink layer disposed on said transparent film layer to provide said package member with an opacity of 15-40%, and a speculum gloss of 2-15.

11. The packaged absorbent product of claim 10, wherein the non-white color layer further includes a matte layer on said non-white color layer and a pearl layer between said matte layer and said transparent film layer.

12. The packaged absorbent product of claim 11, wherein the matte layer is formed by a micro emboss treatment at one surface of the transparent film layer.

13. The packaged absorbent product of claim 11 wherein the non-white color layer further includes a color layer disposed between the transparent film layer and the pearl layer.

14. A packaged absorbent product, comprising:
 (a) at least one absorbent article having a body surface and a garment surface; and
 (b) a package for containing the absorbent article therein, the package being formed by a package member having at least one surface; said package member being formed from a polyolefin film containing at least one filler; wherein the amount of filler in said polyolefin film provides said package member with an opacity of 15-40%; and further wherein said at least one surface has a mechanical or chemical treatment to provide a speculum gloss of 2-15;
 c) the package member including a transparent film layer and a non-white color layer disposed on the transparent film layer.

15. The packaged absorbent product of claim 14 wherein said surface treatment provides said package member with a matte finish.

16. The packaged absorbent product of claim 14 wherein said surface treatment is a micro emboss treatment.

17. The packaged absorbent product of claim 14 wherein said non-white color layer includes a matte layer disposed on the transparent film and a pearl layer disposed between said matte layer and said transparent film.

18. The packaged absorbent product of claim 17 wherein said non-white color layer includes a color layer disposed between the pearl layer and the transparent film layer.

19. The packaged absorbent product of claim 1 wherein said package member contains a translucent area.

\* \* \* \* \*